United States Patent [19]

Russell et al.

[11] Patent Number: 5,422,427
[45] Date of Patent: Jun. 6, 1995

US005422427A

[54] PNEUMOCOCCAL FIMBRIAL PROTEIN A

[75] Inventors: Harold Russell, Atlanta; Jacquelyn Sampson, College Park; Steven P. O'Connor, Roswell, all of Ga.

[73] Assignee: The United States of America is represented by the United States Department of Health and Human Services, Washington, D.C.

[21] Appl. No.: 791,377

[22] Filed: Sep. 17, 1991

[51] Int. Cl.$^6$ .................... C07K 14/00; C07K 16/00; C07K 17/00
[52] U.S. Cl. .................... 530/350; 530/300; 530/324; 530/325; 530/326; 530/327; 530/328; 530/329; 530/330; 530/402; 530/825
[58] Field of Search ............... 530/350, 402, 825, 300, 530/330, 329, 328, 327, 326, 325, 324

[56] References Cited

U.S. PATENT DOCUMENTS

| | | | |
|---|---|---|---|
| 4,762,713 | 8/1988 | Anderson | 424/92 |
| 4,894,362 | 1/1990 | Yamaguchi et al. | 514/12 |
| 5,037,760 | 8/1991 | Smith et al. | 435/320.1 |
| 5,130,417 | 7/1992 | Stanley, Jr. et al. | 530/350 |

FOREIGN PATENT DOCUMENTS

0206852AI 12/1986 European Pat. Off. .
0429816AI 6/1991 European Pat. Off. .

OTHER PUBLICATIONS

Harold Russell et al., "Monoclonal Antibody Recognizing a Species-Specific Protein from *Streptococcus pneumoniae*" Journal of Clinical Microbiology, vol. 28, pp. 2191-2195, Oct. 1990.

Ganeshkumar et al., "Nucleotide Sequence of a Gene Coding for a Saliva-Binding Protein (SsaB) from *Streptococcus sanguis* 12 and Possible Role of the Protein in Coaggregation with Actinomyces", *Inspection and Immunity*, vol. 59, No. 3, 1093-1099, Mar. 1991.

Clarke-Lewis et al (1986) Science 231: 134-139.
Caruthers (1985) Science 230: 281-285.
Science (1988) 240: 362.
Fenno, et al. (1989) Infection & Immunity 57: 3527-3533.
Fives-Taylor et al. (1987) Infection & Immunity 55: 123-128.
Russell, et al. (1990) Journal of Clinical Microbiology 28: 2191-2195.
Russell, et al. (1990) Abstracts of the Annual Meeting of the American Society for Microbiology 90: 436.
Sampson (et al) (1991) Abstracts of the Annual Meeting of the American Society for Microbiology 91: 97.

*Primary Examiner*—Keith C. Furman
*Assistant Examiner*—Hyosuk Kim
*Attorney, Agent, or Firm*—Needle & Rosenberg

[57] ABSTRACT

The present invention relates, in general, to pneumococcal fimbrial protein A. In particular, the present invention relates to a DNA segment encoding a pneumococcal fimbrial protein A gene; polypeptides encoded by said DNA segment; recombinant DNA molecules containing the DNA segment; cells containing the recombinant DNA molecule; a method of producing a pneumococcal fimbrial protein A polypeptide; antibodies specific to pneumococcal fimbrial protein A; and a method of measuring the amount of pneumococcal fimbrial protein A in a sample.

4 Claims, 3 Drawing Sheets

PNEUMOCOCCAL FIMBRIAL PROTEIN A

BACKGROUND OF THE INVENTION

1. Field of the Invention

The present invention relates, in general, to pneumococcal fimbrial protein A (PfpA). In particular, the present invention relates to a DNA segment encoding a pneumococcal fimbrial protein A gene (pfpA); polypeptides encoded by the DNA segment; recombinant DNA molecules containing the DNA segment; cells containing the recombinant DNA molecule; a method of producing a pneumococcal fimbrial protein A polypeptide; antibodies specific to pneumococcal fimbrial protein A; and a method of measuring the amount of pneumococcal fimbrial protein A in a sample.

2. Background Information

Disease caused by *Streptococcus pneumoniae* (pneumococcus) is an important cause of morbidity and mortality in the United States and developing countries (Sorensen, J. et al. (1986) Scand. J. Infect. Dis. 18:329-335; Wall, R. A. et al. (1986) Bull. WHO 64-4:553-558; Walsh, J. A., and K. S. Warren (1979) N. Eng. J. Med. 301:967-974; Williams, W. W. et al. (1988) Ann. Intern. Med. 108:616-625; Yolken, R. H. et al. (1984) J. Clin. Microbiol. 20:802-805). Pneumococcal disease is very prevalent among the very young, the elderly, and immunocompromised persons. Despite its prevalence, diagnosis of the disease continues to be a problem.

Several tests have been developed to detect pneumococcus antigens and/or antibodies as a means of diagnosing pneumococcus infections (Coonrod, J. D., and M. W. Rytel (1973) J. Lab Clin. Med. 81:778-786; Holmberg, H. et al. (1985) J. Clin. Microbiol. 22:111-115; Ingram, D. L. et al. (1983) J. Clin. Microbiol. 18:1119-1121; Jalonen, E. et al. (1989) J. Infect. 19:127-134; Kanclerski, K. et al. (1988) J. Clin. Microbiol. 26-1:96-100; Makela, P. H. (1982) Scand. J. Infect. Dis. Suppl. 36:111-113; Perlino, C. A. (1984) J. Infect. Dis. 150:139-144; Sippel, J. E. et al. (1984) J. Clin. Microbiol. 20:884-886; Whitby, M. et al. (1985) J. Clin. Pathol. 38:341-344; Yolken, R. H. et al. (1984) J. Clin. Microbiol. 20:802-805). The sensitivity of existing antigen detection tests utilizing body fluids such as serum and urine, remains very low (Ajello, G. W. et al. (1987) J. Clin. Microbiol. 25:1388-1391; Anhalt, J. P., and P. K. W. Yu (1975) J. Clin. Microbiol. 2:510-515; Bartram, C. E. Jr. et al. (1974) J. Lab. Clin. Med. 83:591-598; Congeni, B. L. et al. (1984) Ped. Infect. Dis. 3:417-419; Coonrod, J. D. (1983) Proceedings of the American Journal of Medicine Symposium, Jul. 28, 1983, Am. J. Med. 75:85-92; Coovadia, Y. B. and K. K. Naidu (1985) J. Clin. Pathol. 38:561-564; Dilworth, J. A. (1975) J. Clin. Microbiol. 2:453-455; Doskeland, S. O., and B. P. Berdal (1980) J. Clin. Microbiol. 11:380-384; Martin, S. J. et al. (1987) J. Clin. Microbiol. 25:248-250), except for antigen detection in cerebrospinal fluids (Henrichsen, J. et al. (1980) J. Clin. Microbiol. 11:589-592; Ingram, D. L. et al. (1983) J. Clin. Microbiol. 18:1119-1121; Lenthe-Eboa, S. et al. (1987) Eur. J. Clin. Microbiol. 6:28-34; Tilton, R. C. et al. (1984) J. Clin. Microbiol. 20:231-234; Yolken, R. H. et al. (1984) J. Clin. Microbiol. 20:802-805). The measurement of antibody response to pneumolysin by enzyme immunoassay (ELISA) appears to be promising for presumptive etiologic diagnosis (Jalonen, E. et al. (1989) J. Infect. 19:127-134; Kalin, M. et al. (1987) J. Clin. Microbiol. 25:226-229; Kanclerski, K. et al. (1988) J. Clin. Microbiol. 26-1:96-100), but the sensitivity and specificity of the test need improvement.

Although a positive blood culture is diagnostic for pneumococcus disease, most patients with bacterial pneumonia do not have bacteremia (Austrian, R. (1974) Prev. Med. 3:443-445; Austrian, R., and I. Gold (1964) Ann. Intern. Med. 60:759-776; Kalin, M. and A. A. Lindberg (1983) Scand. J. Infect. Dis. 15:247-255). The value of sputum cultures has also been questioned because of contamination of the specimens with pharyngeal flora that can include pneumococci (Barrett-Cooner, E. (1971) Ann. Rev. Resp. Dis. 103:845-848). Thus, clinical laboratories are rarely successful in establishing a firm bacterial etiology for those patients with respiratory infections diagnosed presumptively as pneumococcus pneumonia. Researchers have been in constant search for immunodiagnostic markers or tests to aid in the early diagnosis of pneumococcus infections.

SUMMARY OF THE INVENTION

It is a general object of this invention to provide pneumococcal fimbrial protein A (PfpA) (a 37-kilodalton protein).

It is a specific object of this invention to provide a DNA segment which encodes a pneumococcal fimbrial protein A gene (pfpA).

It is a further object of the invention to provide a polypeptide corresponding to a pneumococcal fimbrial protein A gene (pfpA).

It is another object of the invention to provide a recombinant DNA molecule comprising a vector and a DNA segment encoding a pneumococcal fimbrial protein A gene (pfpA).

It is a further object of the invention to provide a cell that contains the above-described recombinant molecule.

It is another object of the invention to provide a method of producing a polypeptide encoding a pneumococcal fimbrial protein A gene (pfpA).

It is a further object of the invention to provide antibodies having binding affinity to a pneumococcal fimbrial protein A gene (pfpA), or a unique portion thereof.

It is a further object of the invention to provide a method of measuring the amount of pneumococcal fimbrial protein A in a sample.

Further objects and advantages of the present invention will be clear from the description that follows.

In one embodiment, the present invention relates to a DNA segment coding for a polypeptide comprising an amino acid sequence corresponding to a pneumococcal fimbrial protein A gene.

In another embodiment, the present invention relates to a polypeptide free of proteins with which it is naturally associated and comprising an amino acid sequence corresponding to a pneumococcal fimbrial protein A gene.

In a further embodiment, the present invention relates to a recombinant DNA molecule comprising a vector and a DNA segment that codes for a polypeptide comprising an amino acid sequence corresponding to a pneumococcal fimbrial protein A gene.

In yet another embodiment, the present invention relates to a cell that contains the above-described recombinant DNA molecule.

In a further embodiment, the present invention relates to a method of producing a polypeptide comprising an amino acid sequence corresponding to a pneumococcal fimbrial protein A gene.

In yet another embodiment, the present invention relates to an antibody having binding affinity to a polypeptide encoding a pneumococcal fimbrial protein A gene, or a unique portion thereof.

In a further embodiment, the present invention relates to a method of measuring the amount of pneumococcal fimbrial protein A in a sample, comprising contacting the sample with the above-described antibodies and measuring the amount of immunocomplexes formed between the antibodies and any pneumococcal fimbrial protein A in the sample.

DETAILED DESCRIPTION OF THE INVENTION

Figure 1:
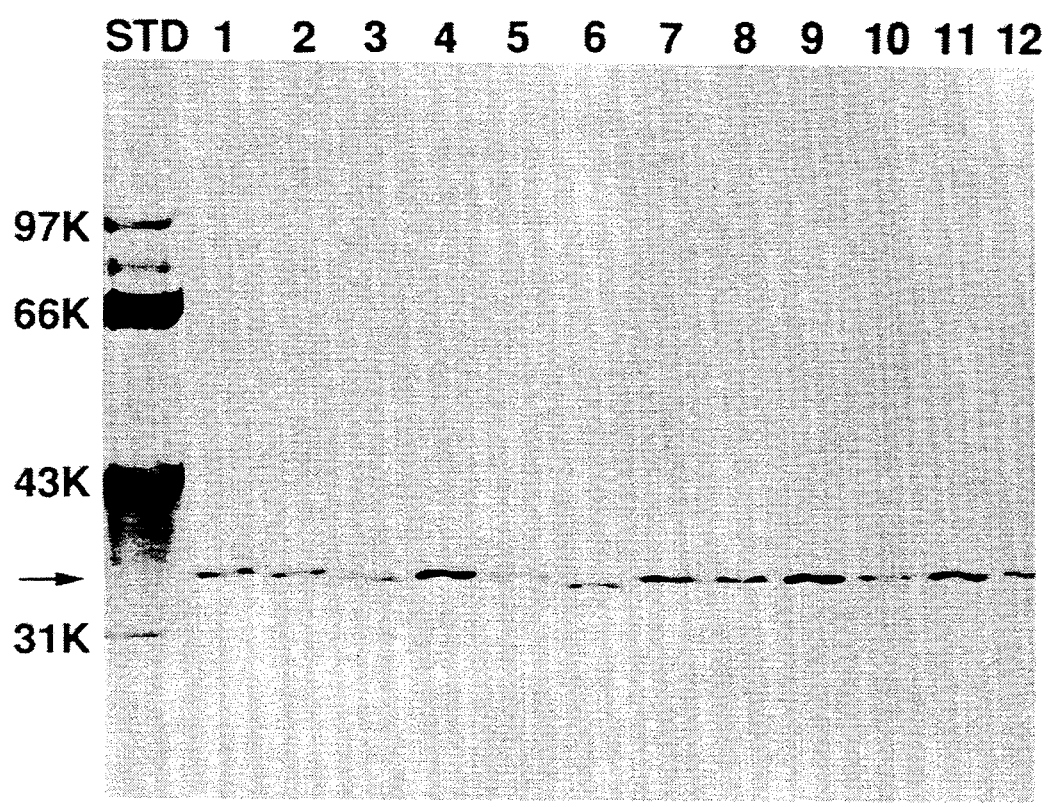
FIG. 1. Immunoblot of S. pneumoniae whole-cell antigen preparations with pneumococcus MAbs. Protein standards (STD) (in kilodaltons) and different serotypes of S. pneumoniae are shown. Lanes: 1, serotype 3; 2, serotype 6B; 3, serotype 7F; 4, serotype 8; 5, serotype 9V; 6, serotype 10A; 7, serotype 11A; 8, serotype 12F; 9, serotype 15B; 10, serotype 19A; 11, serotype 19F; 12, serotype 22F. The MAbs revealed an antigen at 37 kDa (arrow) in all serotypes tested.

In one embodiment, the present invention relates to a DNA segment coding for a polypeptide comprising an amino acid sequence corresponding to pneumococcal fimbrial protein A, or at least 5 contiguous amino acids thereof. In one preferred embodiment, the DNA segment comprises the sequence shown in SEQ ID NO:1, allelic or species variation thereof, or at least 15 contiguous nucleotides thereof (preferably, at least 20, 30, 40, or 50 contiguous nucleotides thereof). In a further preferred embodiment, the DNA segment encodes the amino acid sequence set forth in SEQ ID NO:2, allelic or species variation thereof, or at least 5 contiguous amino acids thereof (preferably, at least 5, 10, 15, 20, 30 or 50 contiguous amino acids thereof).

In a further embodiment, the present invention relates to a polypeptide free of proteins with which it is naturally associated or a polypeptide bound to a solid support and comprising an amino acid sequence corresponding to pneumococcal fimbrial protein A, or at least 5 contiguous amino acids thereof (preferably, at least 5, 10, 15, 20, 30 or 50 contiguous amino acids thereof). In one preferred embodiment, the polypeptide comprises the amino acid sequence set forth in SEQ ID NO:2, or allelic or species variation thereof equivalent thereto (for example, immunologically or functionally, equivalent thereto), or at least 5 contiguous amino acids thereof (preferably, at least 5, 10, 15, 20, 30 or 50 contiguous amino acids thereof).

In another embodiment, the present invention relates to a recombinant DNA molecule comprising a vector (for example plasmid or viral vector) and a DNA segment (as described above) coding for a polypeptide corresponding to pneumococcal fimbrial protein A, as described above. In a preferred embodiment, the encoding segment is present in the vector operably linked to a promoter.

In a further embodiment, the present invention relates to a cell containing the above described recombinant DNA molecule. Suitable host cells include procaryotes (such as bacteria, including E. coli) and both lower eucaryotes (for example yeast) and higher eucaryotes (for example, mammalian cells). Introduction of the recombinant molecule into the cell can be effected using methods known in the art.

In another embodiment, the present invention relates to a method of producing a polypeptide having an amino acid sequence corresponding to pneumococcal fimbrial protein A comprising culturing the above-described cell under conditions such that the DNA segment is expressed and the polypeptide thereby produced and isolating the polypeptide.

In yet another embodiment, the present invention relates to an antibody having binding affinity for pneumococcal fimbrial protein A, or a unique portion thereof. In one preferred embodiment, pneumococcal fimbrial protein A comprises the amino acid sequence set forth in SEQ ID NO:2, allelic or species variation thereof, or at least 5 contiguous amino acids thereof (preferably, at least 5, 10, 15, 20, 30 or 50 contiguous amino acids thereof).

Antibodies (monoclonal or polyclonal) can be raised to pneumococcal fimbrial protein A, or unique portions thereof, in its naturally occuring form and in its recombinant form. Binding fragments of such antibodies are also within the scope of the invention.

Pneumococcal fimbrial protein A may be joined to other materials, particularly polypeptides, as fused or covalently joined polypeptides to be used as immunogens. Pneumococcal fimbrial protein A or its fragments may be fused or covalently linked to a variety of immunogens, such as keyhole limpet hemocyanin, bovine serum albumin, tetanus toxoid, etc. See for example, Microbiology, Hoeber Medical Division (Harper and Row, 1969), Landsteiner, Specificity of Serological Reactions (Dover Publications, New York, 1962) and Williams et al., Methods in Immunology and Immunochemistry, Vol. 1 (Academic Press, New York, 1967), for descriptions of methods of preparing polyclonal antisera. A typical method involves hyperimmunization of an animal with an antigen. The blood of the animal is then collected shortly after the repeated immunizations and the gamma globulin is isolated.

In some instances, it is desirable to prepare monoclonal antibodies from various mammalian hosts. Description of techniques for preparing such monoclonal antibodies may be found in Stites et al., editors, Basic and Clinical Immunology, (Lange Medical Publications, Los Altos, Calif., Fourth edition) and references cited therein, and in particular in Kohler and Milstein in Nature 256:495–497 (1975), which discusses one method of generating monoclonal antibodies.

In another embodiment, the present invention relates to a hybridoma which produces a monoclonal antibody or binding fragment thereof having binding affinity for pneumococcal fimbrial protein A. In one preferred embodiment, the pneumococcal fimbrial protein A has the amino acid sequence set forth in SEQ ID NO:2, allelic or species variation thereof, or at least 5 contiguous amino acids thereof (preferably, at least 5, 10, 15, 20, 30 or 50 contiguous amino acids thereof). In another preferred embodiment, the hybridoma comprises 1E-7A3D7C2.

In yet another embodiment, the present invention relates to a diagnostic kit comprising:
i) at least one of the above-described monoclonal antibodies, and
ii) a conjugate comprising a binding partner of said monoclonal antibody and a label.

In a further embodiment, the present invention relates to a diagnostic kit comprising a conjugate comprising:
i) at least one of the above-described monoclonal antibodies, and
ii) a label.

In a further embodiment, the present invention relates to a method of measuring the amount of pneumococcal fimbrial protein A in a sample, comprising contacting the sample with the above-described antibodies and measuring the amount of immunocomplexes formed between the antibodies and any pneumococcal fimbrial protein A in the sample. Methods of measuring the amount of immunocomplexes formed can be those well known in the art, such as RIA, ELISA, and direct and indirect immunoassays.

In another embodiment, the present invention relates to a vaccine comprising the above-identified polypeptides. The presently used commercial vaccine, Pneumovax, is a mixture of 23 capsular polysaccharides from S. pneumoniae. The vaccine is efficacious in adults but not effective in children less than two years of age. Since the polypeptides of the present invention are proteins, they can be used to protect against pneumococcal disease in children and adults. In one preferred embodiment, the polypeptides describe-above, may be conjugated to components of the existing commercial vaccine. Preliminary data indicate that some children less than two years of age produce antibodies to the pneumococcal fimbrial protein A (the 37-kDa protein).

The present invention is described in further detail in the following non-limiting Examples.

EXAMPLES

The following protocols and experimental details are referenced in the Examples that follow:

Bacterial Strains

The S. pneumoniae strain R36A was kindly provided by D. E. Briles (University of Alabama at Birmingham). Twenty-four serotypes of S. pneumoniae were provided by R. Facklam, Centers for Disease Control (CDC), Atlanta, Ga. These serotypes are 1, 2, 3, 4, 5, 6A, 6B, 7F, 8, 9N, 9V, 10A, 11F, 11A, 12F, 14, 15B, 18C, 19A, 19F, 20, 22F, 23F, and 33F. Enterococcus avium, E. casseliflavus, and E. gallinarum were also provided by R. Facklam. Anaerobic bacteria were obtained from V. R. Dowell, CDC. These included Bacteroides asaccharolyticus, B. fragilis, B. intermedius, B. thetaiotaomicron, Eubacterium lentum, Fusobacterium necrophorum, F. nucleatum, Peptostreptococcus anaerobius, P. asaccharolyticus, Propionibacterium acnes, and Staphylococcus saccharolyticus. Branhamella catarrhalis and Bordetella parapertussis were obtained from R. Weaver, CDC. Mycobacterium tuberculosis was provided by R. C. Good, CDC. R. Barnes, CDC, provided Chlamydia pneumoniae. The following remaining bacteria were from the stock collection of the Immunology Laboratory, CDC: Bordetella pertussis, Enterobacter aerogenes, E. agglomerans, E. cloacae, E. gergoviae, Escherichia coli, Klebsiella pneumoniae, Haemophilus influenzae (types a-f), Legionella micdadei, L. pneumophila, Mycoplasma pneumoniae, Pseudomonas aeruginosa, Serratia marcescens, Staphylococcus aureus, Streptococcus agalactiae, S. equisimilis, S. pyogenes, and group G streptococci.

Production of MAbS

Female BALB/c mice were immunized with whole cell suspensions of S. pneumoniae R36A, a rough derivative of the capsular type 2 strain D39 (Avery, O. T. et al. (1944) J. Exp. Med. 79:137-157). The mice were immunized by intravenous injection three times and intraperitoneal injection one time. The maximum number of cells injected at any time was $10^8$. Fusion was done on day 25 by using standard procedures (Clafin, L., and K. Williams (1978) Curr. Top. Microbiol. Immunol. 81:107-109). Spleen cells of 4 mice were fused with Sp2/0-Ag14 myeloma cells (Schulman, M. et al. (1978) Nature (London) 276:269-270). Culture fluids of the growing hybridomas were tested for antibodies to S. pneumoniae whole cells in an ELISA. A clone designated 1E7A3D7C2 was one of 10 selected for further study. Further references to MAbs in this article refer to hybridoma clone 1E7A3D7C2.

ELISA

Screening of hybridoma culture supernatants was done by ELISA. U-bottom microtitration plates (Costar, Cambridge, Mass.) were sensitized with 50 μl of S. pneumoniae whole cell suspension ($10^9$ CFU/ml) diluted 1:4,000 in 0.1M carbonate buffer, pH 9.6, and kept for 16 h at 4° C. The plates were washed 5 times with 0.9% NaCl containing 0.05% Tween 20 (NaCl-T). Culture supernatants (50 μl) from the fusion plates were added to 50 μl of a solution containing 2% bovine serum albumin (BSA), 10% normal rabbit serum, 0.3% Tween-20, and 0.02% Merthiolate in phosphate buffered saline (PBS), pH 7.2, (ELISA diluent) (Wells, D. E. et al. (1987) J. Clin. Microbiol. 25:516-521) in the plates and were incubated for 30 min at 37° C. The plates were washed 5 times with NaCl-T. Fifty microliters of goat anti-mouse immunoglobulin horseradish peroxidase conjugate, diluted in ELISA diluent was added to each well. The plates were incubated for 30 min at 37° C. The plates were washed, and 50 μl of 3,3',5,5'-tetramethylbenzidine (0.1 mg/ml in 0.1M sodium acetate, 0.1M citric acid [pH 5.7] with 0.005% hydrogen peroxide) was added to each well and incubated for 30 min at 37° C. The reaction was stopped by adding 1 ml of 4M $H_2SO_4$ and the optical density was read on a Dynatech ELISA Reader (Dynatech Laboratories, Inc., Alexandria, Va.) at 450 nm. An optical density of >0.200 was considered positive.

SDS-PAGE and Immunoblot Analysis

Sodium dodecyl sulfate-polyacrylamide gel electrophoresis (SDS-PAGE) was performed by the method of Tsang et al. (Tsang, V. C. W. et al. (1983) Methods Enzymol. 92:377-391), using an 8% acrylamide resolving gel. Equal volumes of sample buffer (5% SDS-10% 2-mercaptoethanol-20% glycerol in 0.01M Tris HCL, [pH 8.0]) and cell suspension containing 2.4 μg protein per μl were mixed, heated at 100° C. for 5 min, and a 5-μl portion was applied to 1 of 15 wells. If the final protein content of the portion of sample to be tested was <1.2 μg/μl, a volume up to 10 μl of sample was applied to achieve a final concentration of 6 μg of protein per well. Protein concentrations were determined by the method of Markwell et al. (Markwell, M. A. et al. (1978) Anal. Biochem. 87:206-210), with BSA as the standard.

Proteins separated by SDS-PAGE were either silver stained by the method of Morrissey (Morrissey, J. H. (1981) Anal. Biochem. 117:307-310) or electroblotted onto nitrocellulose (Schleicher & Schnell, Inc., Keene, N.H.). The immunoblot procedure was done according to the method of Tsang et al. (Tsang, V. C. W. et al. (1983) Methods Enzymol. 92:377–391) with slight modifications. The blots were given three 5-min washes with PBS, pH 7.2, containing 0.3% Tween-20 and were gently agitated overnight (16 h) at 25° C. The blots were blocked for 1 h with casein-thimerosal buffer (CTB) (Kenna, J. G. et al. (1985) J. Immunol. Meth. 85:409–419). After three rinses with CTB, the blots were exposed to goat anti-mouse immunoglobulin horseradish peroxidase conjugate (Bio-Rad Laboratories, Richmond, Calif.) for 2 h at 25° C. Conjugate dilutions (1:2,000) were made in CTB. The blots were again rinsed three times with CTB and exposed to 3-3'diaminobenzadine-4-hydrochloride in PBS, pH 7.2 (0.5 mg/ml), with 0.003% $H_2O_2$ for 5 min at 25° C. Reactivity was expressed as a visible colored band on the nitrocellulose paper. Low-molecular-mass protein standards (Bio-Rad) were used in PAGE and immunoblotting. Rabbit antisera to the protein standards were used to develop the standards (Carlone, G. M. (1986) Anal. Biochem. 155:89–91). Molecular masses were calculated by the method of Neville and Glossman (Neville, D. M., and H. Glossman (1974) Methods Enzymol. 32:92–102) using appropriate molecular mass standards.

IFA

A bacterial suspension containing approximately 400–500 CFU per field (10 μl) was allowed to dry at room temperature on each well of acetone-resistant, 12-well (5 mm diameter), glass slides (25×75 mm) (Cel-Line Associates, Newfield, N.J.). The slides were then immersed in acetone for 10 min and air dried at room temperature. MAbs were added to the slides, which were incubated for 30 min at 37° C. After incubation, the slides were gently rinsed with PBS and soaked twice at 5-min intervals, blotted on filter paper, and air dried at room temperature. Fluorescein-labeled rabbit anti-mouse immunoglobulin (courtesy of W.F.Bibb, CDC) was then added, and the slides were incubated for 30 min at 37° C. They were then washed twice with PBS and gently blotted on filter paper. Slides were covered with carbonate-buffered mounting fluid, pH 9.0, and cover slips and were then read with a Leitz Dialux 20 fluorescence microscope equipped with a HBO-100 mercury incident light source, an I cube filter system, a 40x dry objective lens, and 6.3x binoculars (E. Leitz, Inc., Rockleigh, N.J.).

Immunoelectron Microscopy

Pneumococcal cells were washed two times with PBS and fixed in a mixture of 1% paraformaldehyde-0.1% glutaraldehyde (freshly made) for 20 min at 4° C. The cells were dehydrated in a graded alcohol series and then in a 1:1 mixture of absolute ethanol and Lowicryl K4M (Ladd Research Industries, Inc.,Burlington, Vt.) for 1 h at 4° C. The cells were pelleted and suspended in a 1:2 mixture of absolute ethanol and Lowicryl K4M for 1 h at 4° C. They were again pelleted and suspended in Lowicryl K4M (undiluted) for 16 h at 4° C.

The cells were transferred to fresh Lowicryl K4M two times during the next 24-hour period. The Lowicryl K4M-treated cells were imbedded in gelatin capsules, which were placed inside a box lined with aluminum foil. The capsules were hardened by holding them, in the box, 35 cm from a short-wave UV light source for 72 h at −20° C. The box was brought to room temperature, and the capsules were allowed to continue hardening for up to 14 days.

Samples of the capsule were cut into 100-μm thin sections and picked up on nickel grids. Grids containing the sample were placed on a droplet of ovalbumin solution in PBS containing sodium azide (E.Y. Laboratories, Inc., San Mateo, Calif.) for 5 min. The grids (wet) were transferred to a solution of primary MAbs diluted in a solution of BSA reagent (1% BSA in PBS containing 0.1% Triton X-100, Tween 20, and sodium azide) (E.Y. Laboratories) and incubated for 1 h at room temperature or 18 to 48 h at 4° C. in a moist chamber. For antibody binding controls, other grids were wetted with MAbs against *Legionella pneumophila*. The grids were rinsed two times with PBS and incubated on droplets of goat anti-mouse IgG-labeled colloidal gold particles (20 μm) (E.Y. Laboratories) for 1 h at room temperature. The grids were rinsed two times and poststained with osmium tetroxide, uranyl acetate, and lead citrate. The grids were examined with a Philips 410 transmission electron microscope.

EXAMPLE 1

Monoclonal Antibodies

Hybridoma clone 1E7A3D7C2 produced MAbs that reacted with a 37-kilodalton (kDa) protein antigen (pneumococcal fimbrial protein A) found in *S. pneumoniae*. The MAbs reacted with an antigen fractionated in SDS-PAGE, yielding a single immunoblot band. This indicates that the MAb reacted with epitopes found only on the 37-kDa antigen (pneumococcal fimbrial protein A).

The MAbs produced by the immunization of mice with pneumococcal cells reacted with all pneumococcal strains tested (24 serotypes) to yield a sensitivity of 100%. For specificity, 55 different nonpneumococcal strains of bacteria that can also cause respiratory infections (Donowitz, G. R., and G. L. Mandell (1985) In: Principles and practices in infectious diseases, 2nd ed. (G. L. Mandell, R. G. Douglas, and J. E. Bennett, ed.) John Wiley & Sons, Inc., New York, pp. 394–404) were tested for antigens reacting with the MAbs. The latter strains represented 19 genera and 36 species of bacteria. None of the strains tested reacted with the pneumococcal MAbs, thus yielding a specificity of 100%

Of 44 patients known to have pneumococcus disease, 34 (77%) had antibodies that reacted with the 37-kDa antigen (pneumococcal fimbrial protein A) by Western immunoblot (FIG. 1).

Figure 2:
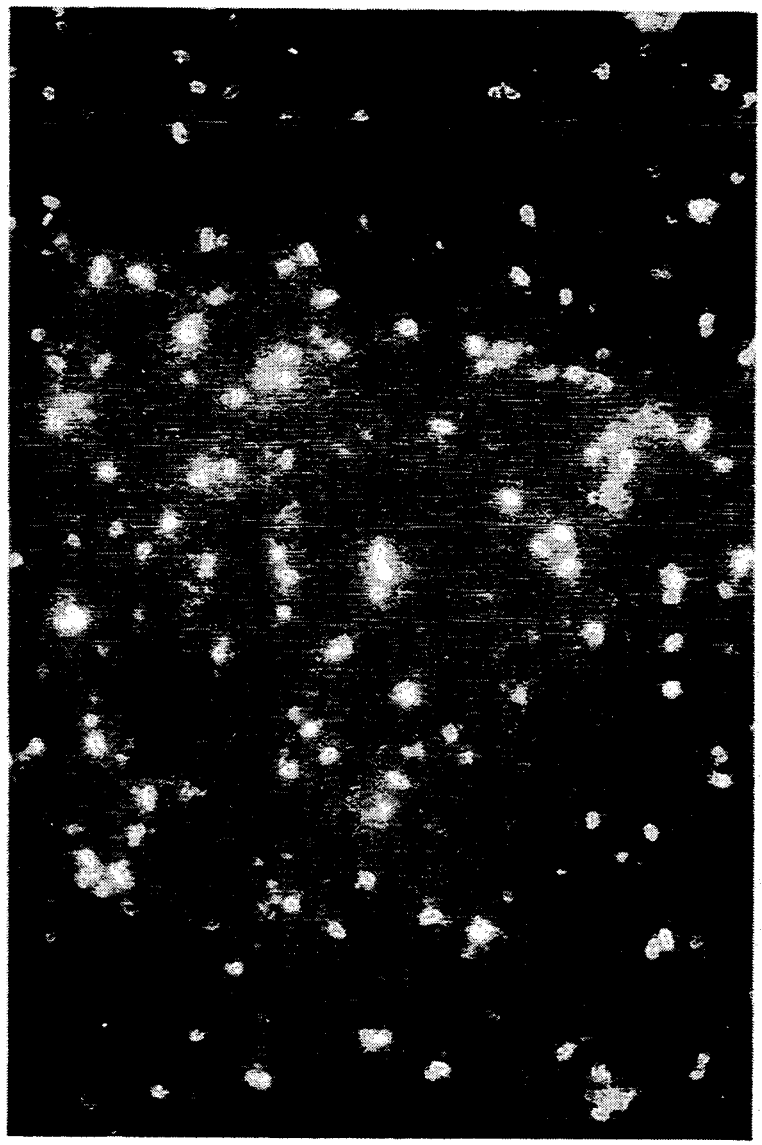
FIG. 2. Immunofluorescence assay staining of S. pneumoniae cells with pneumococcal MAbs.

The MAbs reacted with whole pneumococcal cells to yield a positive test result in both the ELISA and IFA. FIG. 2 shows the bright immunofluorescence of whole pneumococcus cells stained by the MAbs and fluorescein-labeled anti-mouse immunoglobulin in the IFA. Results from both the ELISA and the IFA indicate that the antigen has exposed epitopes on the surface of the cell or that the immunoglobulin and other immunologic reagents are able to penetrate the pneumococcal cell walls.

Several strains of group A streptococci were tested for immunofluorescence after reacting with the pneumococcus MAbs. None of the heterologous bacterial cells fluoresced in this test, indicating that the IFA reaction was specific for pneumococcus cells.

Figure 3:
FIG. 3. Transmission electron microscopy of S. pneumoniae R36A after embedding, cutting, reacting with MAbs, and staining with gold-labeled goat anti-mouse immunoglobulin.

To further determine the location on the cell of the 37-kDa antigen (pneumococcal fimbrial protein A) epitopes reacting with the MAbs, immunolabeling experiments were performed. FIG. 3 shows that the cells were typical of gram-positive cocci in the process of division. The figure also shows the reaction of MAbs and colloidal gold-labeled anti-mouse immunoglobulin G with thin sections of whole pneumococcal cells. A large portion of the antigen appears to be intracellular since there is no coating or layering of the labeled MAbs around the cell. The large patch of colloidal gold staining indicates that the MAbs bound antigen located inside the cell wall. There was no colloidal gold binding to control pneumococci that were exposed to the MAbs against *L. pneumophila*.

EXAMPLE 2

Cloning of the Pneumococcal Fimbrial Protein A Gene

*Streptococcus pneumoniae* DNA digested with restriction enzyme Sau3A1 was ligated to BamHI digested pUC13 and transformed into *E. coli* TB1. Recombinant clones were identified by colony immunoblot using the 37-kDa monoclonal antibody. The plasmid pSTR3-1 is an example of the pneumococcal fimbrial protein A gene cloned into pUC13.

All publications mentioned hereinabove are hereby incorporated in their entirety by reference. Additionally, Russell et al. (October 1990), J. of Clin. Microbiol. 28:2191–2195 is hereby incorporated in its entirety by reference.

While the foregoing invention has been described in some detail for purposes of clarity and understanding, it will be appreciated by one skilled in the art from a reading of this disclosure that various changes in form and detail can be made without departing from the true scope of the invention and appended claims.

---

What is claimed is:

1. A polypeptide free of the proteins with which it is naturally associated comprising the amino acid sequence of pneumococcal fimbrial protein A set forth in SEQ ID NO:2, or an allelic variation thereof.

2. The polypeptide according to claim 1, wherein said polypeptide comprises the amino acid sequence set forth in SEQ ID NO:2.

3. The polypeptide of claim 1 wherein the polypeptide is bound to a solid support.

4. The polypeptide according to claim 3, wherein said polypeptide comprises the amino acid sequence set forth in SEQ ID NO:2.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 1175 base pairs
        ( B ) TYPE: nucleic acid
        ( C ) STRANDEDNESS: double
        ( D ) TOPOLOGY: linear ( i x ) FEATURE:
        ( A ) NAME/KEY: CDS
        ( B ) LOCATION: 243..1172

( x i ) SEQUENCE DESCRIPTION: SEQ ID NO:1:

```
CTCATCACAC  CCGCTGCGAC  AGCCTATCTC  TATGCCAATA  GCCTCTGGTC  CATGATGCTC         60

CTTTCATCCG  GATTAGGTGC  CCTAGCCTCT  ATCCTAGGAC  TCTTTATCGG  CTACAGTTTC        120

AACATCGCCG  TCGGGTCTTG  TATCGTCCTC  ACTTCTGCCA  TCTTCTTTCT  CATCAGCTTC        180

TTTATCGCTC  CTAAGCAGAG  AAAGAATAAG  CACGCTCTTT  CACCTCATTA  AAGGAGAAAC        240

AC  ATG  AAA  AAA  ATC  GCT  TCT  GTC  CTC  GCC  CTC  TTT  GTG  GCG  CTC  TTG        287
    Met  Lys  Lys  Ile  Ala  Ser  Val  Leu  Ala  Leu  Phe  Val  Ala  Leu  Leu
     1              5                       10                      15

TTC  GGC  CTG  TTG  GCC  TGC  AGC  AAA  GGC  ACT  TCT  TCC  AAG  TCC  TCA  TCC        335
Phe  Gly  Leu  Leu  Ala  Cys  Ser  Lys  Gly  Thr  Ser  Ser  Lys  Ser  Ser  Ser
                    20                      25                      30

GAT  AAA  TTG  AAG  GTG  GTT  ACC  ACC  AAC  TCC  ATC  CTT  GCC  GAT  ATC  ACC        383
Asp  Lys  Leu  Lys  Val  Val  Thr  Thr  Asn  Ser  Ile  Leu  Ala  Asp  Ile  Thr
                35                      40                      45

AAA  AAT  ATC  GCT  GGG  GAT  AAA  ATC  GAG  CTC  CAC  AGT  ATT  GTA  CCT  GTC        431
Lys  Asn  Ile  Ala  Gly  Asp  Lys  Ile  Glu  Leu  His  Ser  Ile  Val  Pro  Val
            50                      55                      60

GGT  CAA  GAT  CCC  CAC  GAG  TAC  GAA  CCG  CTC  CCA  GAA  GAT  GTC  AAA  AAA        479
Gly  Gln  Asp  Pro  His  Glu  Tyr  Glu  Pro  Leu  Pro  Glu  Asp  Val  Lys  Lys
        65                      70                      75

ACT  TCA  CAA  GCA  GAC  CTG  ATC  TTC  TAC  AAT  GGG  ATC  AAC  CTC  GAA  ACG        527
Thr  Ser  Gln  Ala  Asp  Leu  Ile  Phe  Tyr  Asn  Gly  Ile  Asn  Leu  Glu  Thr
 80                      85                      90                      95

GGT  GGC  AAT  GCT  TGG  TTT  ACC  AAA  TTG  GTC  AAA  AAT  GCC  AAT  AAA  GTA        575
Gly  Gly  Asn  Ala  Trp  Phe  Thr  Lys  Leu  Val  Lys  Asn  Ala  Asn  Lys  Val
                    100                     105                     110

GAA  AAC  AAG  GAC  TAT  TTC  GCT  GCC  AGC  GAT  GGC  GTA  GAG  GTC  ATC  TAC        623
Glu  Asn  Lys  Asp  Tyr  Phe  Ala  Ala  Ser  Asp  Gly  Val  Glu  Val  Ile  Tyr
                115                     120                     125
```

| | | | | | | | | | | | | | | | | |
|---|---|---|---|---|---|---|---|---|---|---|---|---|---|---|---|---|
| CTG | GAA | GGC | CAA | AAC | CAA | GCT | GGA | AAA | GAA | GAC | CCT | CAC | GCT | TGG | CTC | 671 |
| Leu | Glu | Gly | Gln | Asn | Gln | Ala | Gly | Lys | Glu | Asp | Pro | His | Ala | Trp | Leu | |
| | | 130 | | | | 135 | | | | | 140 | | | | | |
| AAT | CTC | GAA | AAC | GGG | ATT | ATC | TAC | GCT | AAA | AAC | ATT | GCC | AAA | CAA | TTA | 719 |
| Asn | Leu | Glu | Asn | Gly | Ile | Ile | Tyr | Ala | Lys | Asn | Ile | Ala | Lys | Gln | Leu | |
| | 145 | | | | | 150 | | | | | 155 | | | | | |
| ATC | GCC | AAA | GAT | CCA | AAA | AAT | AAG | GAC | TTC | TAC | GAA | AAA | AAT | CTA | GCA | 767 |
| Ile | Ala | Lys | Asp | Pro | Lys | Asn | Lys | Asp | Phe | Tyr | Glu | Lys | Asn | Leu | Ala | |
| 160 | | | | | 165 | | | | | 170 | | | | | 175 | |
| GCC | TAC | ACT | GAA | AAA | CTC | AGC | AAG | CTA | GAC | CAA | GAA | GCC | AAG | CAA | GCA | 815 |
| Ala | Tyr | Thr | Glu | Lys | Leu | Ser | Lys | Leu | Asp | Gln | Glu | Ala | Lys | Gln | Ala | |
| | | | | 180 | | | | | 185 | | | | | 190 | | |
| TTC | AAT | AAC | ATC | CCA | GCA | GAG | AAG | AAG | ATG | ATC | GTA | ACC | AGC | GAA | GGT | 863 |
| Phe | Asn | Asn | Ile | Pro | Ala | Glu | Lys | Lys | Met | Ile | Val | Thr | Ser | Glu | Gly | |
| | | | 195 | | | | | 200 | | | | | 205 | | | |
| TGC | TTC | AAG | TAC | TTC | TCC | AAA | GCC | TAC | GGC | GTC | CCA | TCT | GCC | TAT | ATC | 911 |
| Cys | Phe | Lys | Tyr | Phe | Ser | Lys | Ala | Tyr | Gly | Val | Pro | Ser | Ala | Tyr | Ile | |
| | | 210 | | | | | 215 | | | | | 220 | | | | |
| TGG | GAA | ATC | AAC | ACT | GAA | GTA | GAA | GGG | ACA | CCT | GAA | CAA | ATC | AAA | ACG | 959 |
| Trp | Glu | Ile | Asn | Thr | Glu | Val | Glu | Gly | Thr | Pro | Glu | Gln | Ile | Lys | Thr | |
| | 225 | | | | | 230 | | | | | 235 | | | | | |
| CTG | CTA | GAG | AAA | TTG | CGT | CAA | ACC | AAA | GTA | CCG | TCC | CTC | TTT | GTC | GAA | 1007 |
| Leu | Leu | Glu | Lys | Leu | Arg | Gln | Thr | Lys | Val | Pro | Ser | Leu | Phe | Val | Glu | |
| 240 | | | | | 245 | | | | | 250 | | | | | 255 | |
| TCC | AGT | GTC | GAT | GAG | CGT | CCT | ATG | AAA | ACT | GTG | TCT | AAG | GAT | AGC | AAT | 1055 |
| Ser | Ser | Val | Asp | Glu | Arg | Pro | Met | Lys | Thr | Val | Ser | Lys | Asp | Ser | Asn | |
| | | | | 260 | | | | | 265 | | | | | 270 | | |
| ATC | CCT | ATC | TTT | GCA | AAG | ATC | TTT | ACT | GAC | TCG | ATT | GCC | AAA | GAA | GGC | 1103 |
| Ile | Pro | Ile | Phe | Ala | Lys | Ile | Phe | Thr | Asp | Ser | Ile | Ala | Lys | Glu | Gly | |
| | | | 275 | | | | | 280 | | | | | 285 | | | |
| GAA | GAA | GGC | GAC | AGC | TAC | TAC | AGC | ATG | ATG | AAA | TGG | AAT | TTG | GAG | AAA | 1151 |
| Glu | Glu | Gly | Asp | Ser | Tyr | Tyr | Ser | Met | Met | Lys | Trp | Asn | Leu | Glu | Lys | |
| | | 290 | | | | | 295 | | | | | 300 | | | | |
| ATC | GCA | GAA | GGT | TTG | AAC | AAA | TAA | | | | | | | | | 1175 |
| Ile | Ala | Glu | Gly | Leu | Asn | Lys | | | | | | | | | | |
| | 305 | | | | | 310 | | | | | | | | | | |

( 2 ) INFORMATION FOR SEQ ID NO:2:

( i ) SEQUENCE CHARACTERISTICS:
        ( A ) LENGTH: 310 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Met | Lys | Lys | Ile | Ala | Ser | Val | Leu | Ala | Leu | Phe | Val | Ala | Leu | Leu | Phe |
| 1 | | | | 5 | | | | | 10 | | | | | 15 | |
| Gly | Leu | Leu | Ala | Cys | Ser | Lys | Gly | Thr | Ser | Ser | Lys | Ser | Ser | Ser | Asp |
| | | | 20 | | | | 25 | | | | | 30 | | | |
| Lys | Leu | Lys | Val | Val | Thr | Thr | Asn | Ser | Ile | Leu | Ala | Asp | Ile | Thr | Lys |
| | | 35 | | | | | 40 | | | | | 45 | | | |
| Asn | Ile | Ala | Gly | Asp | Lys | Ile | Glu | Leu | His | Ser | Ile | Val | Pro | Val | Gly |
| | 50 | | | | | 55 | | | | | 60 | | | | |
| Gln | Asp | Pro | His | Glu | Tyr | Glu | Pro | Leu | Pro | Glu | Asp | Val | Lys | Lys | Thr |
| 65 | | | | | 70 | | | | | 75 | | | | | 80 |
| Ser | Gln | Ala | Asp | Leu | Ile | Phe | Tyr | Asn | Gly | Ile | Asn | Leu | Glu | Thr | Gly |
| | | | | 85 | | | | | 90 | | | | | 95 | |
| Gly | Asn | Ala | Trp | Phe | Thr | Lys | Leu | Val | Lys | Asn | Ala | Asn | Lys | Val | Glu |
| | | | 100 | | | | | 105 | | | | | 110 | | |

-continued

| | | | | | | | | | | | | | |
|---|---|---|---|---|---|---|---|---|---|---|---|---|---|
| Asn | Lys 115 | Asp | Tyr | Phe | Ala | Ala | Ser 120 | Asp | Gly | Val | Val 125 | Ile | Tyr | Leu |
| Glu | Gly 130 | Gln | Asn | Gln | Ala | Gly 135 | Lys | Glu | Asp | Pro | His 140 | Ala | Trp | Leu | Asn |
| Leu 145 | Glu | Asn | Gly | Ile | Ile 150 | Tyr | Ala | Lys | Asn | Ile 155 | Ala | Lys | Gln | Leu | Ile 160 |
| Ala | Lys | Asp | Pro | Lys 165 | Asn | Lys | Asp | Phe | Tyr 170 | Glu | Lys | Asn | Leu | Ala 175 | Ala |
| Tyr | Thr | Glu | Lys 180 | Leu | Ser | Lys | Leu | Asp 185 | Gln | Glu | Ala | Lys | Gln 190 | Ala | Phe |
| Asn | Asn | Ile 195 | Pro | Ala | Glu | Lys | Lys 200 | Met | Ile | Val | Thr | Ser 205 | Glu | Gly | Cys |
| Phe | Lys 210 | Tyr | Phe | Ser | Lys | Ala 215 | Tyr | Gly | Val | Pro | Ser 220 | Ala | Tyr | Ile | Trp |
| Glu 225 | Ile | Asn | Thr | Glu | Val 230 | Glu | Gly | Thr | Pro | Glu 235 | Gln | Ile | Lys | Thr | Leu 240 |
| Leu | Glu | Lys | Leu | Arg 245 | Gln | Thr | Lys | Val | Pro 250 | Ser | Leu | Phe | Val | Glu 255 | Ser |
| Ser | Val | Asp | Glu 260 | Arg | Pro | Met | Lys | Thr 265 | Val | Ser | Lys | Asp | Ser 270 | Asn | Ile |
| Pro | Ile | Phe 275 | Ala | Lys | Ile | Phe | Thr 280 | Asp | Ser | Ile | Ala | Lys 285 | Glu | Gly | Glu |
| Glu | Gly 290 | Asp | Ser | Tyr | Tyr | Ser 295 | Met | Met | Lys | Trp | Asn 300 | Leu | Glu | Lys | Ile |
| Ala 305 | Glu | Gly | Leu | Asn | Lys 310 | | | | | | | | | | |